(12) United States Patent
Pratt et al.

(10) Patent No.: US 11,839,474 B2
(45) Date of Patent: Dec. 12, 2023

(54) MAGNETOENCEPHALOGRAPHY (MEG) PHANTOMS FOR SIMULATING NEURAL ACTIVITY

(71) Applicant: HI LLC, Los Angeles, CA (US)

(72) Inventors: Ethan Pratt, Santa Clara, CA (US); Hooman Mohseni, Wilmette, IL (US); Stephen Garber, Santa Monica, CA (US)

(73) Assignee: HI LLC, Los Angeles, CA (US)

( * ) Notice: Subject to any disclaimer, the term of this patent is extended or adjusted under 35 U.S.C. 154(b) by 867 days.

(21) Appl. No.: 16/884,672

(22) Filed: May 27, 2020

(65) Prior Publication Data

US 2020/0381128 A1   Dec. 3, 2020

Related U.S. Application Data

(60) Provisional application No. 62/910,248, filed on Oct. 3, 2019, provisional application No. 62/855,820, filed on May 31, 2019.

(51) Int. Cl.
*A61B 5/245* (2021.01)
*G09B 23/30* (2006.01)
(Continued)

(52) U.S. Cl.
CPC .............. *A61B 5/245* (2021.01); *A61B 8/587* (2013.01); *G01R 33/26* (2013.01); *G09B 23/30* (2013.01); *A61B 2576/026* (2013.01)

(58) Field of Classification Search
CPC ... A61B 5/245; A61B 8/587; A61B 2576/026; G09B 23/30; G01R 33/26; G01R 33/326; G01R 33/4806
See application file for complete search history.

(56) References Cited

U.S. PATENT DOCUMENTS 3,173,082 A   3/1965   Bell et al.
3,257,608 A   6/1966   Bell et al.
(Continued)

FOREIGN PATENT DOCUMENTS

CN   104730484   6/2015
CN   107562188   1/2018
(Continued)

OTHER PUBLICATIONS

Allred, J. C., Lyman, R. N., Kornack, T. W., & Romalis, M. V. (2002). High-sensitivity atomic magnetometer unaffected by spin-exchange relaxation. Physical review letters, 89(13), 130801.
(Continued)

*Primary Examiner* — Steven L Yeninas
(74) *Attorney, Agent, or Firm* — Branch Partners PLLC; Bruce E. Black (57) ABSTRACT

A neural phantom device configured and arranged to produce a magnetic field to simulate a neural signal. The neural phantom device includes a driver having a signal source configured to produce a simulated neural signal, and either i) a carrier wave source configured to produce a carrier wave having a frequency of at least 250 Hz or ii) an optical carrier wave source configured to produce an optical carrier wave, wherein the driver is configured to modulate the simulated neural signal using the carrier wave or optical carrier wave to generate a modulated signal. The neural phantom device also includes a phantom configured to receive the modulated signal, demodulate the modulated signal to recover the simulated neural signal, and generate the magnetic field in response to the simulated neural signal.

20 Claims, 8 Drawing Sheets

(51) Int. Cl.
  *G01R 33/26* (2006.01)
  *A61B 8/00* (2006.01)

(56) References Cited

U.S. PATENT DOCUMENTS

| | | | |
|---|---|---|---|
| 3,495,161 A | 2/1970 | Bell | |
| 3,501,689 A | 3/1970 | Robbiano | |
| 3,513,381 A | 5/1970 | Happer, Jr. | |
| 4,193,029 A | 3/1980 | Cioccio et al. | |
| 4,951,674 A | 8/1990 | Zanakis et al. | |
| 5,189,368 A | 2/1993 | Chase | |
| 5,192,921 A | 3/1993 | Chantry et al. | |
| 5,225,778 A | 7/1993 | Chaillout et al. | |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A | 8/1995 | Wikswo, Jr. et al. | |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 5,756,875 A * | 5/1998 | Parker | G01N 29/30 367/13 |
| 5,938,598 A * | 8/1999 | Takeda | G09B 23/286 600/416 |
| 6,144,872 A | 11/2000 | Graetz | |
| 6,339,328 B1 | 1/2002 | Keene et al. | |
| 6,472,869 B1 | 10/2002 | Upschulte et al. | |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 | 5/2006 | Romalis et al. | |
| 7,102,451 B2 | 9/2006 | Happer et al. | |
| 7,145,333 B2 | 12/2006 | Romalis et al. | |
| 7,521,928 B2 | 4/2009 | Romalis et al. | |
| 7,656,154 B2 | 2/2010 | Kawabata et al. | |
| 7,826,065 B1 | 11/2010 | Okandan et al. | |
| 7,872,473 B2 | 1/2011 | Kitching et al. | |
| 7,994,783 B2 | 8/2011 | Ledbetter et al. | |
| 8,054,074 B2 | 11/2011 | Ichihara et al. | |
| 8,212,556 B1 | 7/2012 | Schwindt et al. | |
| 8,258,884 B2 | 9/2012 | Borwick, III et al. | |
| 8,319,156 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |
| 8,587,304 B2 | 11/2013 | Budker et al. | |
| 8,836,327 B2 | 9/2014 | French et al. | |
| 8,906,470 B2 | 12/2014 | Overstolz et al. | |
| 8,941,377 B2 | 1/2015 | Mizutani et al. | |
| 9,026,194 B2 * | 5/2015 | Okada | A61N 1/445 600/407 |
| 9,084,549 B2 | 7/2015 | Desain et al. | |
| 9,095,266 B1 | 8/2015 | Fu | |
| 9,116,201 B2 | 8/2015 | Shah et al. | |
| 9,140,590 B2 | 9/2015 | Waters et al. | |
| 9,140,657 B2 | 9/2015 | Ledbetter et al. | |
| 9,169,974 B2 | 10/2015 | Parsa et al. | |
| 9,244,137 B2 | 1/2016 | Kobayashi et al. | |
| 9,291,508 B1 | 3/2016 | Biedermann et al. | |
| 9,343,447 B2 | 3/2016 | Parsa et al. | |
| 9,366,735 B2 | 6/2016 | Kawabata et al. | |
| 9,383,419 B2 | 7/2016 | Mizutani et al. | |
| 9,395,425 B2 | 7/2016 | Diamond et al. | |
| 9,417,293 B2 | 8/2016 | Schaffer et al. | |
| 9,429,918 B2 | 8/2016 | Parsa et al. | |
| 9,568,565 B2 | 2/2017 | Parsa et al. | |
| 9,575,144 B2 | 2/2017 | Kornack et al. | |
| 9,601,225 B2 | 3/2017 | Parsa et al. | |
| 9,638,768 B2 | 5/2017 | Foley et al. | |
| 9,639,062 B2 | 5/2017 | Dyer et al. | |
| 9,677,905 B2 | 6/2017 | Waters et al. | |
| 9,726,626 B2 | 8/2017 | Smith et al. | |
| 9,726,733 B2 | 8/2017 | Smith et al. | |
| 9,791,536 B1 * | 10/2017 | Alem | G01R 35/005 |
| 9,829,544 B2 | 11/2017 | Bulatowicz | |
| 9,846,054 B2 | 12/2017 | Waters et al. | |
| 9,851,418 B2 | 12/2017 | Wolf et al. | |
| 9,869,731 B1 | 1/2018 | Hovde et al. | |
| 9,915,711 B2 | 3/2018 | Kornack et al. | |
| 9,927,501 B2 | 3/2018 | Kim et al. | |
| 9,948,314 B2 | 4/2018 | Dyer et al. | |
| 9,964,609 B2 | 5/2018 | Ichihara et al. | |
| 9,964,610 B2 | 5/2018 | Shah et al. | |
| 9,970,999 B2 | 5/2018 | Larsen et al. | |
| 9,995,800 B1 | 6/2018 | Schwindt et al. | |
| 10,024,929 B2 | 7/2018 | Parsa et al. | |
| 10,088,535 B1 | 10/2018 | Shah | |
| 10,162,016 B2 | 12/2018 | Gabrys et al. | |
| 10,194,865 B2 | 2/2019 | Le et al. | |
| 10,314,508 B2 | 6/2019 | Desain et al. | |
| 10,371,764 B2 | 8/2019 | Morales et al. | |
| 10,772,561 B2 | 9/2020 | Donaldson | |
| 2003/0122544 A1 * | 7/2003 | Parker | A61B 6/583 324/309 |
| 2004/0232912 A1 | 11/2004 | Tsukamoto et al. | |
| 2005/0007118 A1 | 1/2005 | Kitching et al. | |
| 2005/0046851 A1 | 3/2005 | Riley, Jr. et al. | |
| 2005/0206377 A1 | 9/2005 | Romalis et al. | |
| 2007/0076776 A1 | 4/2007 | Lust et al. | |
| 2007/0120563 A1 | 5/2007 | Kawabata et al. | |
| 2007/0167723 A1 | 7/2007 | Park et al. | |
| 2007/0205767 A1 | 9/2007 | Xu et al. | |
| 2009/0079426 A1 | 3/2009 | Anderson | |
| 2009/0101806 A1 | 4/2009 | Masuda | |
| 2010/0047751 A1 * | 2/2010 | Boers | A61B 5/369 434/267 |
| 2010/0219820 A1 | 9/2010 | Skidmore et al. | |
| 2011/0062956 A1 | 3/2011 | Edelstein et al. | |
| 2012/0112749 A1 | 5/2012 | Budker et al. | |
| 2013/0082700 A1 | 4/2013 | Mizutani et al. | |
| 2013/0082701 A1 | 4/2013 | Mizutani et al. | |
| 2013/0265042 A1 | 10/2013 | Kawabata et al. | |
| 2014/0121491 A1 | 5/2014 | Zhang | |
| 2014/0306700 A1 | 10/2014 | Kamada et al. | |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0378316 A1 | 12/2015 | Parsa et al. | |
| 2016/0061913 A1 | 3/2016 | Kobayashi et al. | |
| 2016/0116553 A1 | 4/2016 | Kim et al. | |
| 2016/0223627 A1 | 8/2016 | Shah et al. | |
| 2016/0291099 A1 | 10/2016 | Ueno | |
| 2016/0313417 A1 | 10/2016 | Kawabata et al. | |
| 2017/0023653 A1 | 1/2017 | Kobayashi et al. | |
| 2017/0023654 A1 | 1/2017 | Kobayashi et al. | |
| 2017/0067969 A1 | 3/2017 | Butters et al. | |
| 2017/0199138 A1 | 7/2017 | Parsa et al. | |
| 2017/0199251 A1 | 7/2017 | Fujii et al. | |
| 2017/0261564 A1 | 9/2017 | Gabrys et al. | |
| 2017/0331485 A1 | 11/2017 | Gobet et al. | |
| 2017/0343617 A1 | 11/2017 | Manickam et al. | |
| 2017/0343695 A1 | 11/2017 | Stetson et al. | |
| 2017/0356969 A1 | 12/2017 | Ueno | |
| 2017/0360322 A1 | 12/2017 | Ueno | |
| 2017/0363695 A1 | 12/2017 | Ueno | |
| 2018/0003777 A1 | 1/2018 | Sorenson et al. | |
| 2018/0033339 A1 * | 2/2018 | Kerins | G09B 23/34 |
| 2018/0038921 A1 | 2/2018 | Parsa et al. | |
| 2018/0100749 A1 | 4/2018 | Waters et al. | |
| 2018/0128885 A1 | 5/2018 | Parsa et al. | |
| 2018/0156875 A1 | 6/2018 | Herbsommer et al. | |
| 2018/0219353 A1 | 8/2018 | Shah | |
| 2018/0238974 A1 | 8/2018 | Shah et al. | |
| 2018/0313908 A1 | 11/2018 | Knappe et al. | |
| 2018/0313913 A1 | 11/2018 | DeNatale et al. | |
| 2018/0372813 A1 | 12/2018 | Bulatowicz et al. | |
| 2019/0391213 A1 | 12/2019 | Alford | |
| 2020/0025844 A1 | 1/2020 | Alford et al. | |
| 2020/0057115 A1 | 2/2020 | Jiménez-Martínez et al. | |
| 2020/0057116 A1 | 2/2020 | Zorzos et al. | |
| 2020/0064421 A1 | 2/2020 | Kobayashi et al. | |
| 2020/0072916 A1 | 3/2020 | Alford et al. | |
| 2020/0088811 A1 | 3/2020 | Mohseni | |

(56) References Cited

U.S. PATENT DOCUMENTS

| | | | |
|---|---|---|---|
| 2020/0241094 A1 | 7/2020 | Alford | |
| 2020/0256929 A1 | 8/2020 | Ledbetter et al. | |
| 2020/0309873 A1 | 10/2020 | Ledbetter et al. | |
| 2020/0334559 A1 | 10/2020 | Anderson et al. | |
| 2020/0341081 A1 | 10/2020 | Mohseni et al. | |
| 2020/0381128 A1 | 12/2020 | Pratt et al. | |
| 2020/0400763 A1 | 12/2020 | Pratt | |
| 2021/0015427 A1 | 1/2021 | Shah et al. | |
| 2021/0063510 A1 | 3/2021 | Ledbetter | |
| 2021/0137400 A1* | 5/2021 | Mirov | A61B 5/319 |
| 2021/0142657 A1* | 5/2021 | Mirov | A61B 5/245 |

FOREIGN PATENT DOCUMENTS

| | | |
|---|---|---|
| CN | 110742607 | 2/2020 |
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, (56) References Cited

OTHER PUBLICATIONS and Svenja Knappe, "Magnetic field imaging with microfabricated optically-pumped magnetometers," Opt. Express 25, 7849-7858 (2017).
Slocum et al., Self-Calibrating Vector Magnetometer for Space, https://esto.nasa.gov/conferences/estc-2002/Papers/B3P4(Slocum).pdf.
Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.
J. A. Neuman, P. Wang, and A. Gallagher, Robust high-temperature sapphire cell for metal vapors, Review of Scientific Instruments, vol. 66, Issue 4, Apr. 1995, pp. 3021-3023.
Borna, Amir, et al. "A 20-channel magnetoencephalography system based on optically pumped magnetometers." Physics in Medicine & Biology 62.23 (2017): 8909.
R. E. Slocum & L. J. Ryan, Design and operation of the minature vector laser magnetometer, Nasa Earth Science Technology Conference 2003.
Schoenmaker, Jeroen & R Pirota, K & Teixeira, Julio. (2013). Magnetic flux amplification by Lenz lenses. The Review of scientific instruments. 84. 085120. 10.1063/1.4819234.
Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.
Masuda, Y & Ino, T & Skoy, Vadim & Jones, G.L. (2005). 3He polarization via optical pumping in a birefringent cell. Applied Physics Letters. 87. 10.1063/1.2008370.
A.B. Baranga et al., An atomic magnetometer for brain activity imaging, Real Time Conference 2005. 14th IEEE—NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al.: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.
Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.
Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.
Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.
Okada, Y.C., Lahteenmäki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649 652 (2007).
Griffith, W.C., Knappe, S. and Kitching, J., "Femtotesla atomic magnetometry in a microfabricated vapor cell." Optics express 18, (26), 27167-27172 (2010).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grón, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamform- (56) References Cited

OTHER PUBLICATIONS ers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.
Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.
Zetter, R., Iivanainen, J. & Parkkonen, L. Optical Co-registration of MRI and On-scalp MEG. Sci Rep 9, 5490 (2019). https://doi.org/10.1038/s41598-019-41763-4.
Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.
Hill RM, Boto E, Rea M, et al. Multi-channel whole-head OPM-MEG: Helmet design and a comparison with a conventional system [published online ahead of print, May 29, 2020]. Neuroimage. 2020;219:116995. doi:10.1016/j.neuroimage.2020.116995.
V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.
Holmes, N., Tierney, T.M., Leggett, J. et al. Balanced, bi-planar magnetic field and field gradient coils for field compensation in wearable magnetoencephalography. Sci Rep 9, 14196 (2019).
N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.
J. M. Leger et. al., In-flight performance of the Absolute Scalar Magnetometer vector mode on board the Swarm satellites, Earth, Planets, and Space (2015) 67:57.
Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.
Gravrand, O., Khokhlov, A., & JL, L. M. (2001). On the calibration of a vectorial 4He pumped magnetometer. Earth, planets and space , 53 (10), 949-958.
Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.
Vrba J, Robinson SE. Signal processing in magnetoencephalography. Methods. 2001;25(2):249-271. doi:10.1006/meth.2001.1238.
Uusitalo M and Ilmoniemi R., 1997, Signal-space projection method for separating MEG or EEG into components. Med. Biol. Comput. (35) 135-140.
Taulu S and Kajola M., 2005, Presentation of electromagnetic multichannel data: the signal space separation method. J. Appl. Phys. (97) 124905 (2005).
Taulu S, Simola J and Kajola M., 2005, Applications of the signal space separation method. IEEE Trans. Signal Process. (53) 3359-3372 (2005).
Taulu S, Simola J., 2006, Spatiotemporal signal space separation method for rejecting nearby interference in MEG measurements. Phys. Med. Biol. (51) 1759-1768 (2006).
Johnson, et al., Magnetoencephalography with a two-color pump-probe, fiber-coupled atomic magnetometer, Applied Physics Letters 97, 243703 2010.
Zhang, et al., Magnetoencephalography using a compact multichannel atomic magnetometer with pump-probe configuration, AIP Advances 8, 125028 (2018).
Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelecctromagnetics Society, Kanazawa, Japan, May 28.29, 2009 (pp. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.
Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.
Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS One 13, No. 5 (May 10, 2018): e0191111.
Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.
Nagel, S., & Spüler, M. (2019). Asynchronous non-invasive high-speed BCI speller with robust non-control state detection. Scientific Reports, 9(1), 8269.
Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.
J. Kitching, "Chip-scale atomic devices," Appl. Phys. Rev. 5(3), 031302 (2018), 39 pages.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.
Zhang Xin et al: "Detection and analysis of MEG signals in occipital region with double-channel OPM sensors", Journal of Neuroscience Methods, Elsevier Science Publisher B. V., Amsterdam, NL, vol. 346, Sep. 17, 2020 (Sep. 17, 2020).

\* cited by examiner

MAGNETOENCEPHALOGRAPHY (MEG) PHANTOMS FOR SIMULATING NEURAL ACTIVITY

CROSS-REFERENCE TO RELATED APPLICATIONS

This application claims the benefit of U.S. Provisional Patent Application Ser. Nos. 62/855,820, filed May 31, 2019, and 62/910,248, filed Oct. 3, 2019, both of which are incorporated herein by reference in their entireties.

FIELD

The present disclosure is directed to the area of phantoms configured to simulate one or more biological signal generators, such as neurons. The present disclosure is also directed to magnetic field measurement systems including systems for magnetoencephalography (MEG) and the inclusion and use of phantoms for operating or calibrating the system.

BACKGROUND

In the nervous system, neurons propagate signals via action potentials. These are brief electric currents which flow down the length of a neuron causing chemical transmitters to be released at a synapse. The time-varying electrical current within an ensemble of the neurons generates a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices.

BRIEF SUMMARY

One embodiment is a neural phantom device configured and arranged to produce a magnetic field to simulate a neural signal. The neural phantom device includes a driver having a signal source configured to produce a simulated neural signal, and a carrier wave source configured to produce a carrier wave having a frequency of at least 250 Hz, wherein the driver is configured to modulate the simulated neural signal using the carrier wave to generate a modulated signal. The neural phantom device also includes a phantom configured to receive the modulated signal, demodulate the modulated signal to recover the simulated neural signal, and generate the magnetic field in response to the simulated neural signal.

In at least some embodiments, the carrier wave has a frequency of at least 1 kHz. In at least some embodiments, the phantom includes a rectifier circuit. In at least some embodiments, the phantom includes a full wave rectifier circuit.

In at least some embodiments, the phantom includes a printed circuit board and electrical components coupled to the printed circuit board. In at least some embodiments, the phantom includes a plurality of printed circuit boards stacked together and electrical component coupled to the printed circuit boards.

In at least some embodiments, the neural phantom device includes a plurality of the phantoms. In at least some embodiments, the neural phantom device includes a plurality of the drivers, wherein each driver is coupled to at least one of the phantoms.

Another embodiments is a neural phantom device configured and arranged to produce a magnetic field to simulate a neural signal. The neural phantom device includes a driver having a signal source configured to produce a simulated neural signal, and an optical carrier wave source configured to produce an optical carrier wave, wherein the driver modulates the simulated neural signal using the optical carrier wave to generate a modulated optical signal. The neural phantom device also includes a phantom configured to receive the modulated optical signal, demodulate the modulated optical signal to recover the simulated neural signal, and generate the magnetic field in response to the simulated neural signal.

In at least some embodiments, the driver includes an electro-optical modulator. In at least some embodiments, the driver include an optical projector. In at least some embodiments, the phantom includes an array of optical detectors. In at least some embodiments, the optical detectors are photodiodes. In at least some embodiments, the neural phantom device includes at least 100 channels. In at least some embodiments, the neural phantom device further includes a transparent medium disposed between the driver and the phantom, wherein the transparent medium is configured to simulate a conductivity of components of a user's head. In at least some embodiments, the optical carrier wave source is a light source.

Yet another embodiment is a magnetic field measurement system that includes any of the neural phantom devices described above; at least one magnetometer; at least one memory; and at least one processor coupled to the at least one memory, the at least one magnetometer, and the neural phantom device.

In at least some embodiments, the processor is configured to perform actions including operating the neural phantom device to at least one simulated neural signal and generate a magnetic field using the phantom of the neural phantom device in response to the simulated neural signal; and receiving, from at least one of the magnetometers, a signal in response to the generated magnetic field.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of phantoms configured to simulate one or more biological signal generators, such as neurons. The present disclosure is also directed to magnetic field measurement systems including systems for magnetoencephalography (MEG) and the inclusion and use of phantoms for operating or calibrating the system.

The phantoms, phantom devices, systems and methods are exemplified herein for MEG applications including the observation or detection of neural signals. It will be understood, however, that the phantoms, phantom devices, systems and methods may be used or adapted for use in observing or detecting other biological and nonbiological signals.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more sources (for example, neural signals or other biological sources). The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a portable or wearable MEG system that can be used outside a magnetically shielded room. Examples of wearable MEG systems are described in U.S. Non-Provisional patent application Ser. No. 16/457,655 which is incorporated herein by reference in its entirety.

Figure 1A:
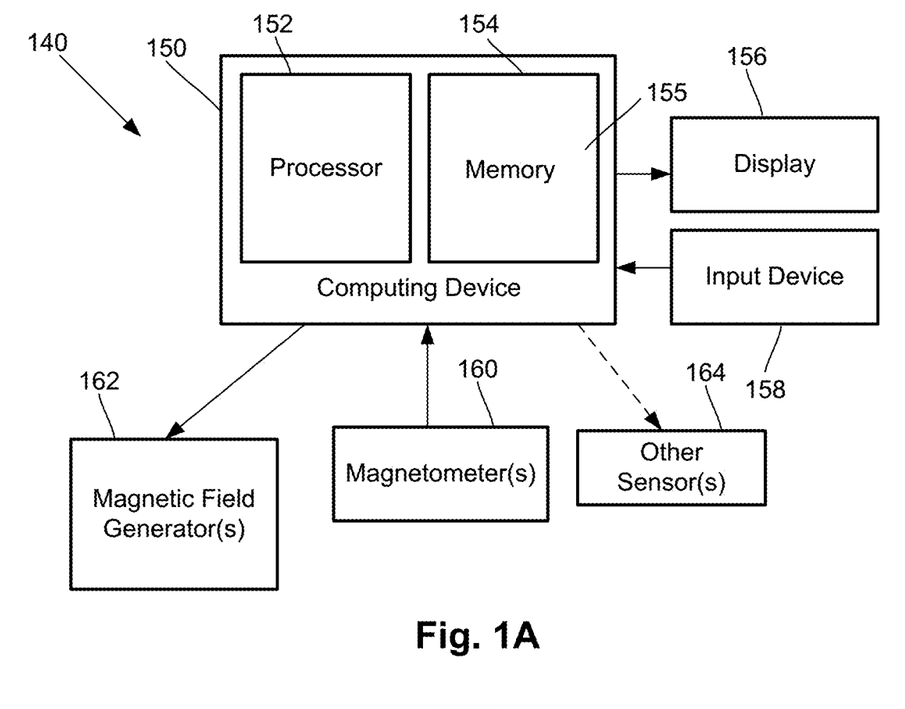
FIG. 1A is a schematic block diagram of one embodiment of a magnetic field measurement system, according to the invention.

A magnetic field measurement system, such as a MEG system, can utilize one or more magnetic field sensors. Magnetometers will be used herein as an example of magnetic field sensors, but other magnetic field sensors may also be used. FIG. 1A is a block diagram of components of one embodiment of a magnetic field measurement system 140. The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions such as instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangement can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems or methods of making such systems or components for such systems are described in U.S. Patent Application Publications Nos. 2020/0072916; 2020/0056263; 2020/0025844; 2020-0057116; 2019/0391213; 2020/0088811; and 2020/0057115; U.S. patent application Ser. Nos. 16/573,394; 16/573,524; 16/679,048; 16/741,593; and Ser. No. 16/752,393, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; and 62/983,406, all of which are incorporated herein by reference in their entireties. Any of these magnetic field systems can be used with the phantoms or neural phantom devices described hereinbelow.

Figure 1B:
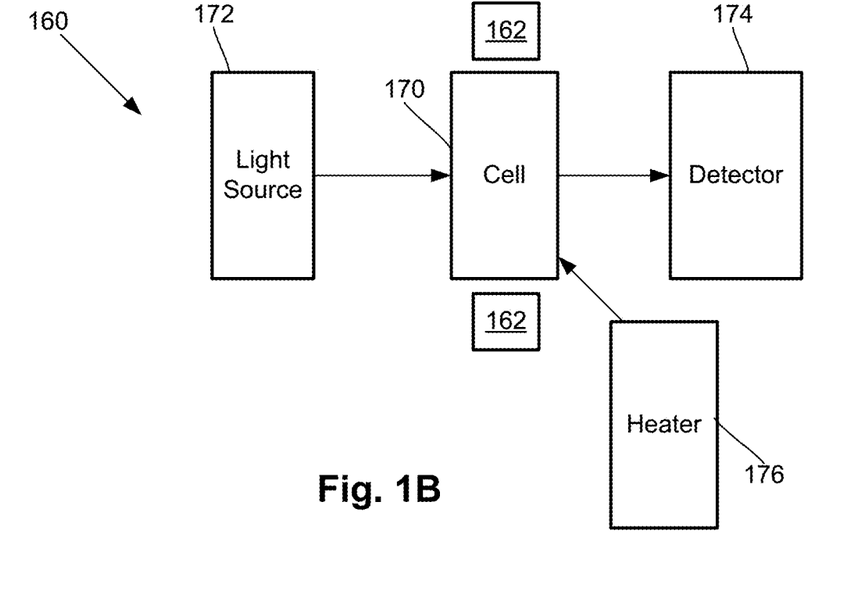
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell" or "vapor cell") such as an alkali metal vapor cell; a heating device 176 to heat the cell 170; a pump light source 172*a*; a probe light source 172*b*; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The pump and probe light sources 172*a*, 172*b* can each include, for example, a laser to, respectively, optically pump the alkali metal atoms and probe the vapor cell. The pump and probe light sources 172*a*, 172*b* may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
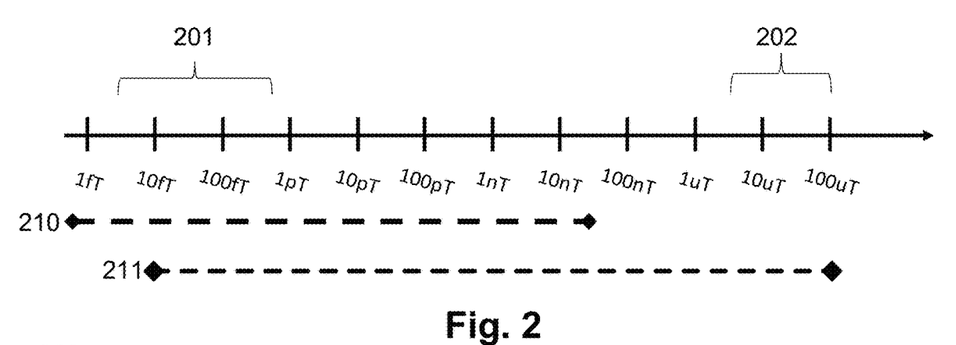
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 μT.

A magnetoencephalography (MEG) phantom is an artificial object that simulates or imitates human brain activity and can be used, for example, to evaluate or calibrate a MEG system. Examples of conventional MEG phantoms can be found at Oyama et al., J. Neuroscience Methods 251, 24-36 (2015) which is incorporated herein by reference. Phantoms can also be used for other magnetometer or magnetic field measurement systems.

If a modeled current dipole is firing somewhere within a spherical conductive medium, then any radial components of the total current path ("radial" being defined with respect to the origin of the sphere) don't generate an external magnetic field (or generate a small magnetic field that can be ignored for many purposes). As one example that utilizes this observation, a dry MEG phantom can include a triangular wire loop, with a vertex at the sphere's origin, and twisted-pair leads exiting from that vertex to form two legs of the triangle. (The overlapping insulated wires may not form a perfect triangle, but with fine gauge wire this arrangement is a reasonable approximation.) The drive current and return current are purely radial, and therefore generate zero (or nearly zero) magnetic field outside the spherical medium. Only the third "tangential" leg of the triangle, which can be formed as a section of wire of desired length, contributes to the external magnetic field.

There are also wet phantoms that use a true volumetric conductor to return the volume currents, and therefore do not rely on the triangular geometry of the current path to eliminate or reduce stray fields. However, the twisted pair excitation wires represent a source of uncompensated magnetic field error and the volume of conductive fluid used in the phantoms can present manufacturability issues.

Although complicated neural paths can—in principle—be constructed from the sums of elementary current dipoles, in practice it may be difficult to pack the "dry triangle loop" elementary phantom dipoles close enough together to give high fidelity for modeling small convoluted neural pathways such as those in the human brain. In addition, high channel counts could result in a relatively large number of excitation wire leads at the exiting cable harness, all of which ideally exit the spherical center of the phantom volume, but, in practice, may result in uncompensated magnetic field error due to deviation from this ideal. Moreover, the excitation leads carry neural current directly between a driver board and the phantom dipole, but cannot be perfectly compensated due to finite wire size effects. This imperfect compensation can lead to substantial phantom inaccuracy.

For neural-activity decoding MEG systems, the MEG phantoms described above may not be sufficiently accurate, representative, or useful. The phantoms for MEG or other applications are provided for the task of spatial source localization with high accuracy or for system error calibration. Therefore, phantom inaccuracy may produce inaccurate results.

In contrast, in at least some embodiments, the phantoms, phantom devices, systems, and methods described hereinbelow can be used to model neural current paths and embody high spatial complexity, with relatively high channel counts, in a format that is easily manufactured. Magnetic field measurement systems, such as MEG systems, which can be used with the phantoms, phantom devices, systems, methods described herein include, but are not limited to, those described in the patent applications cited above. These magnetic field measurement systems (e.g., MEG systems) include sensors, such as optically-pumped magnetometers (OPMs) or other magnetometers, that can measure magnetic fields, such as the neural magnetic fields detected using MEG.

One shortcoming of the conventional MEG phantoms described above is stray fields due to imperfectly compensated excitation currents flowing in the drive leads. As described herein, this shortcoming can be addressed (e.g., reduced or eliminated) by modulating, at a driver (e.g., controller) of a phantom device, a simulated neural signal at a higher frequency either electronically or optically. This modulated signal is delivered from the driver to one or more phantoms. (Multiple phantoms can be provided on a single phantom board or substrate or can be separate from each other.) The MEG sensors, such as OPMs or other magnetometers, cannot detect magnetic fields arising from the modulated signal in transit from the driver/controller because the modulated signal is outside the frequency range of detection by the MEG sensor. The modulated signal is then demodulated locally at the phantom (e.g., at the site of the modeled neuron in the phantom) and the demodulated neural signal flows as an electrical current to produce a selected magnetic field profile in order to simulate a neuron (or group of neurons).

Another shortcoming of conventional MEG phantoms is a limited capability to model large numbers of neurons with direct wire excitation due to cable harness limitations. In contrast, optical embodiments described herein can facilitate a wireless high-channel-count MEG phantom device.

In at least some embodiments, the present phantoms, systems, and methods utilize or go beyond the equivalent current dipole (ECD) model. The ECD model's physical justification arises from the columnar nature of cortical neurons. When a small bundle of neurons fires, the resulting current traverses a short distance where it is then able to return to the source (for charge balance) in a diffuse manner throughout the conductive cerebrospinal fluid (CSF) in the skull.

The equivalent current dipole (ECD) model assigns a neural event to a short linear current path of magnitude j and length L. The current dipole's strength jL has units of A*m and for neural sources can range from approximately 0.1 nA*m to hundreds of nA*m. The return current is distributed spatially throughout the conductive medium inside the skull (a "volume current"). As opposed to the magnetic field generated by a magnetic dipole of characteristic loop size L—which falls off as $r^3$ far away from the loop—the magnetic field from a current dipole falls off as $r^2$. A challenge in making MEG phantoms is associated with how to generate a localized current path with real supply and return currents that don't generate spurious or stray fields.

The spurious or stray fields from the excitation can be reduced or avoided by employing modulation with a high-frequency carrier (either electronic or optical) to shift the frequency of the neural data (or signal) to a band above the responsive bandwidth of the MEG sensors (e.g., OPMs or other magnetometers) such that the sensors cannot detect fields due to the excitation between the driver/controller and the phantom(s). The phantom locally demodulates the excitation and directs the desired low-frequency neural signal (e.g., neural current) into a defined path to simulate neuron(s). In at least some embodiments, the neural signal contains spectral content only up to a neural cutoff frequency of, for example, no more than, for example, 250 Hz, 200 Hz, or 100 Hz. In at least some embodiments, modulation with a high-frequency electronic carrier wave and balanced-pair conductive wires for such transmission, or modulation with an optical carrier wave for wireless transmission, can be used.

In at least some embodiments, demodulation of the excitations near the locations of the desired neural current paths on the brain phantom is used. In at least some embodiments, the demodulator circuits are implemented with relatively small uncompensated current paths following demodulation, to reduce magnetic fields emanating from any conductors except the desired model neural current pathway. In at least some electronic embodiments, the demodulator circuit can be formed of a few discrete passive components. In at least some optical embodiments, the demodulator circuit can be a single photodiode or array of photodiodes.

One of the features of at least some embodiments is the use of distributed sheet conductance layers on a printed circuit board (PCB) to facilitate highly manufacturable MEG phantoms which, at least in some embodiments, are able to produce complex neural-like magnetic fields. In at least some embodiments, there may be some loss of fidelity to the real brain when utilizing a 2D versus a 3D conductor.

Figure 3A:
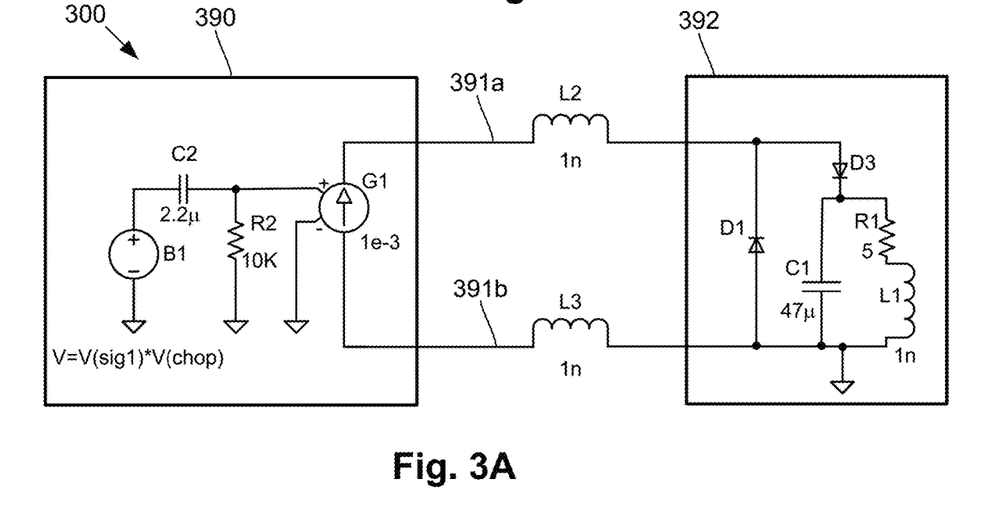
FIGS. 3A and 3B illustrates one embodiment of a circuit diagram for a phantom device, according to the invention.
Figure 3B:
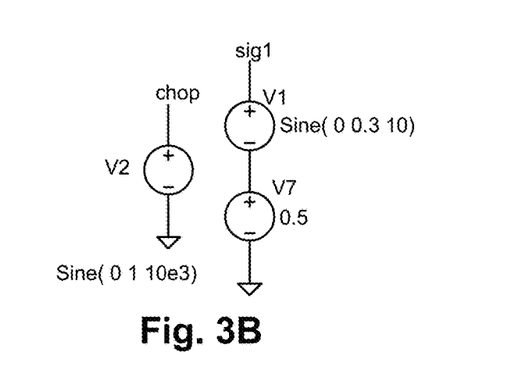

Some embodiments of the phantoms, phantom devices, systems, and methods utilize an electronic implementation. One embodiment of a phantom device 300 is illustrated in FIGS. 3A and 3B and includes a driver 390 (or controller) and a phantom 392. It will be understood that other embodiments can include multiple phantoms which may be coupled to a single driver or may be coupled (individually or in sets) to two or more different drivers. A phantom may simulate a single neuron or group of neurons or multiple individual neurons or groups of neurons.

In at least some embodiments, modulation of the simulated neural signal before transmission from the driver 390 to the phantom 392 is utilized so that spurious magnetic fields due to the transiting modulated signal are shifted in frequency to a band outside the responsive bandwidth of the magnetometer(s) (e.g., sensors).

In the driver 390, a simulated neural signal (V(sig 1) in FIG. 3A produced by V1 in FIG. 3B) is mixed with a carrier wave (V(chop) in FIG. 3A produced by V2 in FIG. 3B) to produce a modulated signal. The frequency of the carrier wave is chosen to be higher than the neural cutoff frequency. The carrier wave frequency can be any suitable frequency such as a frequency of at least 250 Hz, 500 Hz, 1 kHz, 10 kHz, or higher. As an example, a 10 Hz envelope simulated neural signal (V(sig1)) can be combined with a 10 kHz carrier wave (V(chop)).

FIGS. 3A and 3B illustrates one embodiment of a circuit diagram for a phantom device 300 that produces amplitude modulation (AM) in the driver 390 and rectification at the modeled neuron L1 at the phantom 392 in order to reduce or eliminate the effect of stray fields from the wire leads 391a (L2) and 391b (L3). In at least some embodiments, the output current lines from the driver 390 are isolated, balanced, and drive the two wire leads 391a, 391b (which could be a twisted pair) to the phantom 392. There, a diode D3 rectifies the modulated signal and a capacitor C1 shunts the carrier wave current back to the driver 390, while the low-frequency simulated neural signal is directed through the desired neural path (indicated as an inductor L1 in the circuit illustration of FIG. 3A) where it generates a magnetic field that simulates a neural signal. In at least some embodiments, the current of the simulated neural signal returns to the driver 390 through a distributed conductance—for example, a sheet embodied by a 2D layer on a PCB, or a volume embodied by immersing the terminals in a conductive fluid, with suitable encapsulation of the rest of the circuit of the phantom 392. This is similar to a classic AM radio circuit, where the modulated signal on the input traces to each phantom do not generate any low-frequency magnetic fields that would be detected by the MEG sensors (e.g., OPMs or other magnetometers).

In at least some embodiments, the supply current is sourced and sunk entirely at the isolated voltage-controlled current source (VCCS) so that multiple simulated neurons can be laid out on the same PCB board without crosstalk even though they share the common distributed conductance held at ground. The VCCS can alternatively be implemented with a suitable transformer circuit. In at least some embodiments, resistor R2 can be employed to control the compliance voltage of the drive circuit and ensure that stray lead resistance is small compared to the neural path resistance where it can be precisely defined.

Figure 4:
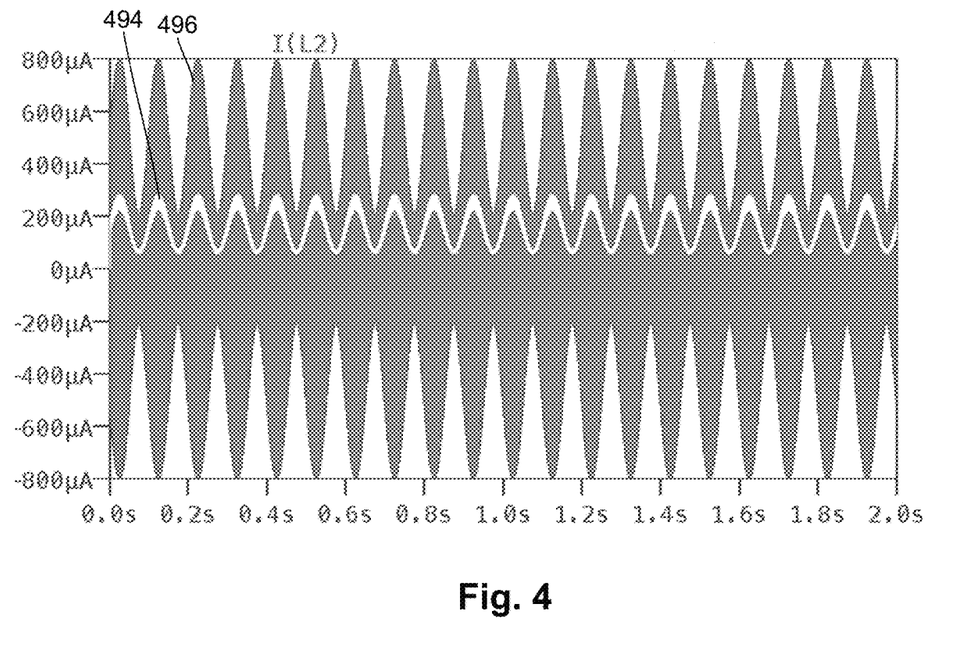
FIG. 4 illustrates AM current with a 10 kHz carrier tone the supply traces, overlaid with the rectified, low-pass filtered simulated neural signal flowing in the model neuron L1 of the phantom device of FIGS. 3A and 3B, according to the invention.

FIG. 4 illustrates AM current with a 10 kHz carrier tone 496 in the supply traces, overlaid with the rectified, low-pass filtered simulated neural signal 494 flowing in the model neuron L1 (FIG. 3A).

Figure 5:
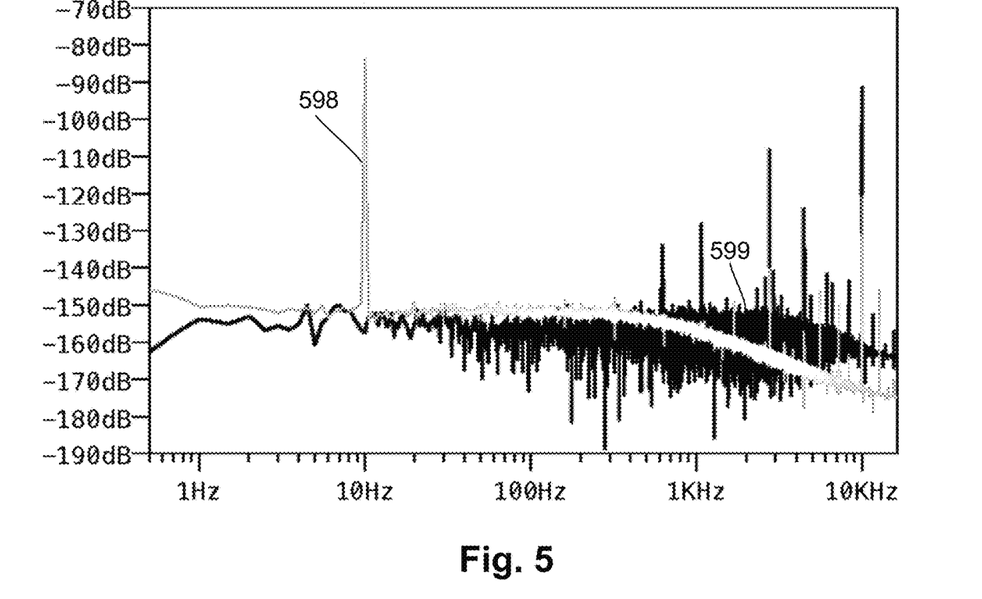
FIG. 5 illustrates simulated spectral content for the phantom device of FIGS. 3A and 3B, according to the invention.

FIG. 5 illustrates simulated spectral content indicating that the magnetometers (which in at least some embodiments are sensitive up to approximately 250 Hz) will see no substantial stray field 599 generated by the leads while the model neuron L1 generates a clean field containing the desired neural signal 598 at 10 Hz.

Figure 6A:
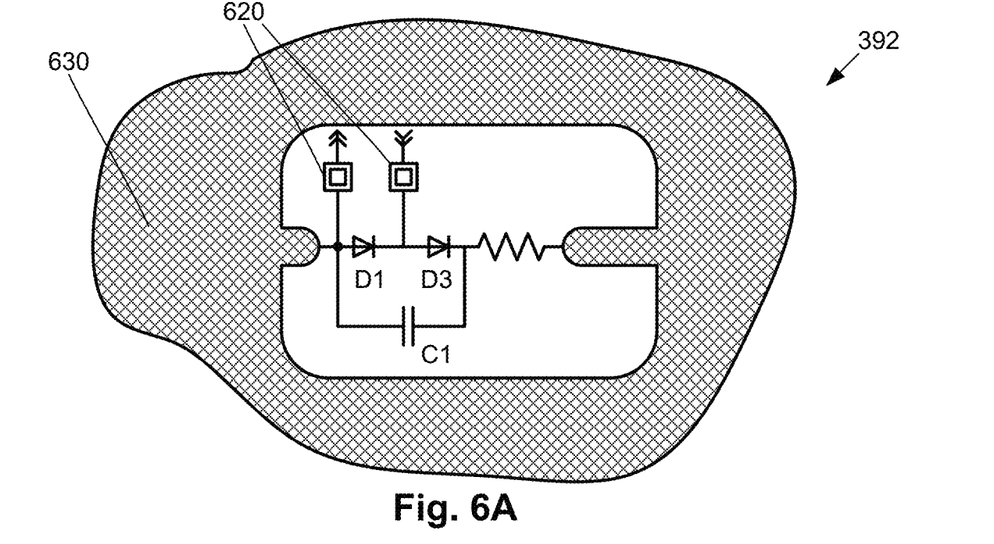
FIGS. 6A to 6C schematically illustrates X, Y, and Z orientations, respectively, of one embodiment of a phantom, according to the invention.
Figure 6B:
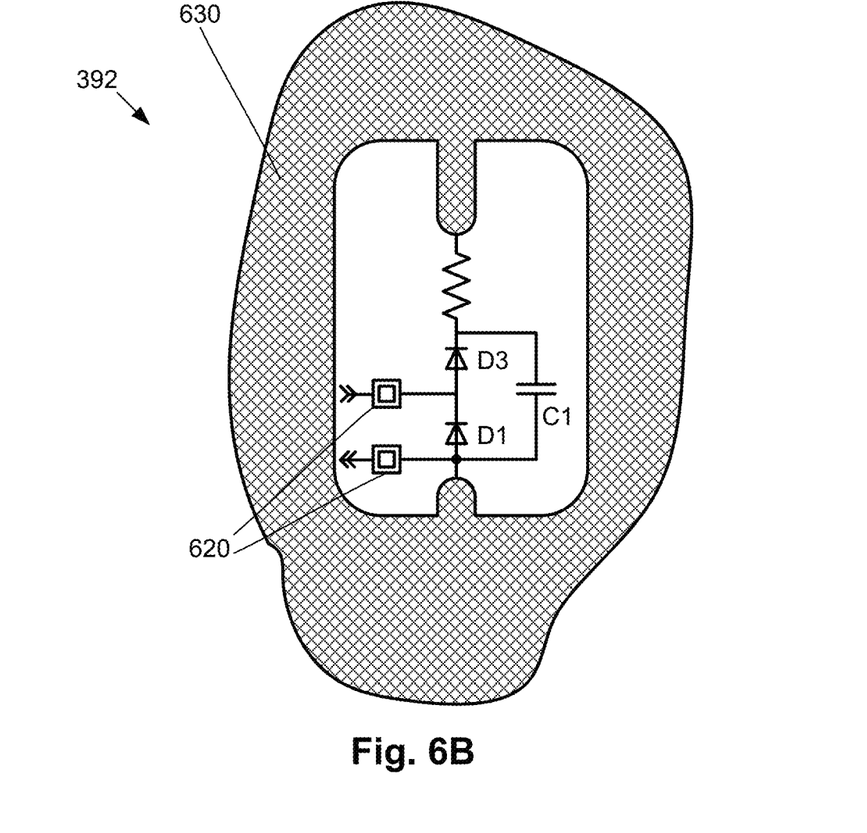
Figure 6C:
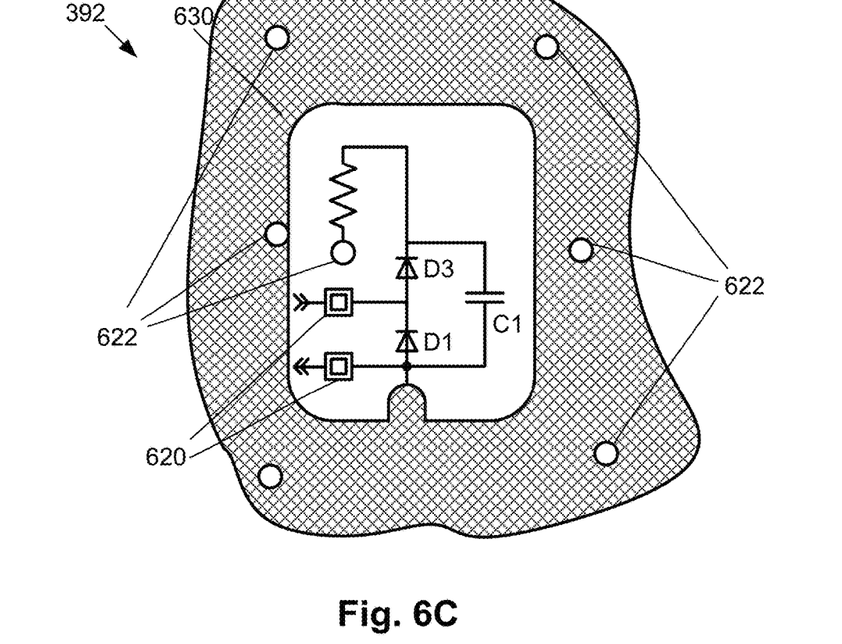
Figure 6D:
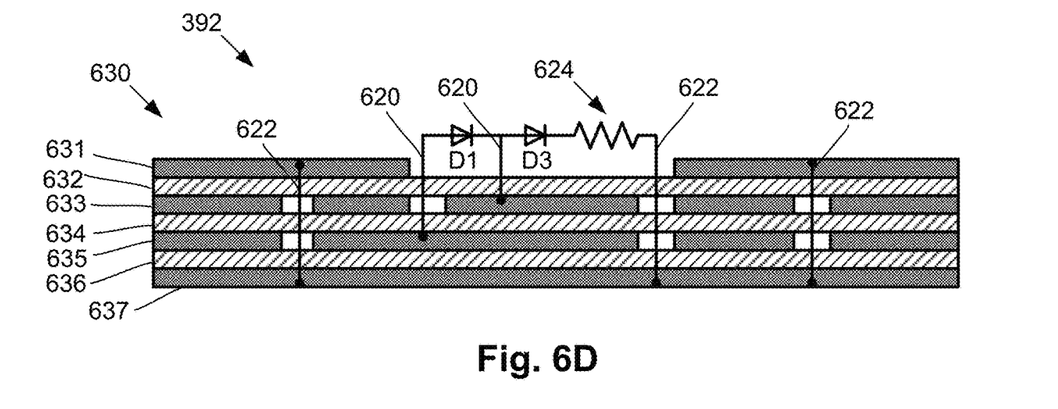
FIG. 6D schematically illustrates a layer diagram for the phantom of FIGS. 6A to 6C, according to the invention.

FIGS. 6A, 6B, and 6C illustrate X, Y, and Z orientations, respectively, of one embodiment of a phantom 390 using a dry PCB elementary current dipole neural rectifier, where X and Y are in the plane of a printed circuit board 630 (PCB), and Z is the PCB-normal direction. FIG. 6D is a layer view that illustrates the layers of the PCB 630 including conductive layers 631, 633, 635, 637 (or pours) and non-conductive substrates 632, 634, 636, as well as vias 620, 622 through the PCB. First vias 620 indicate that the amplitude-modulated input/output currents are taken on inner conductive layers 633, 635 to the edge of the PCB 630 where they can mate to cable connectors for interfacing to the driver 390 (FIG. 3A). Second vias 622 connect the top-and-bottom conductive layers 631, 637 to each other. The Z neural current dipole is represented as the via 622 connected directly to the drive resistor 624. In this embodiments, the length of the current dipole is then roughly equivalent to the PCB 630 thickness, which can easily be made approximately 6 mm thick or any other suitable thickness. On the top layer of the Z phantom, all traces are naturally running in the XY plane, which means that loops should be compensated wherever possible (indicated by flipping the resistor around).

Figure 7A:
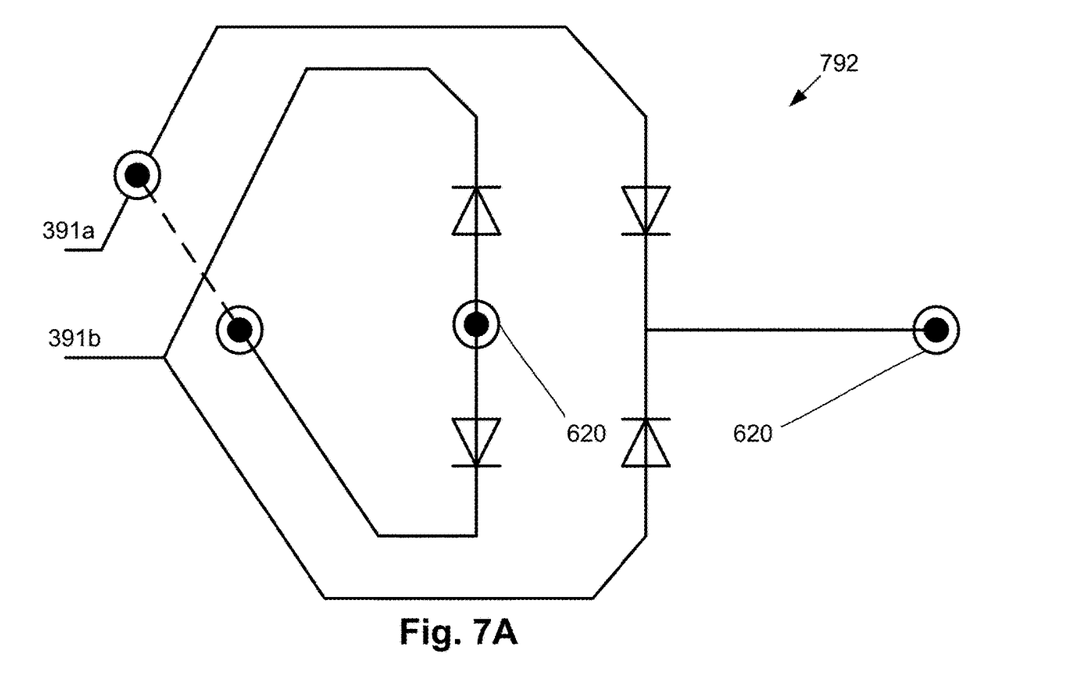
FIG. 7A is a circuit diagram of one embodiment of a phantom utilizing a full wave rectifier, according to the invention.
Figure 7B:
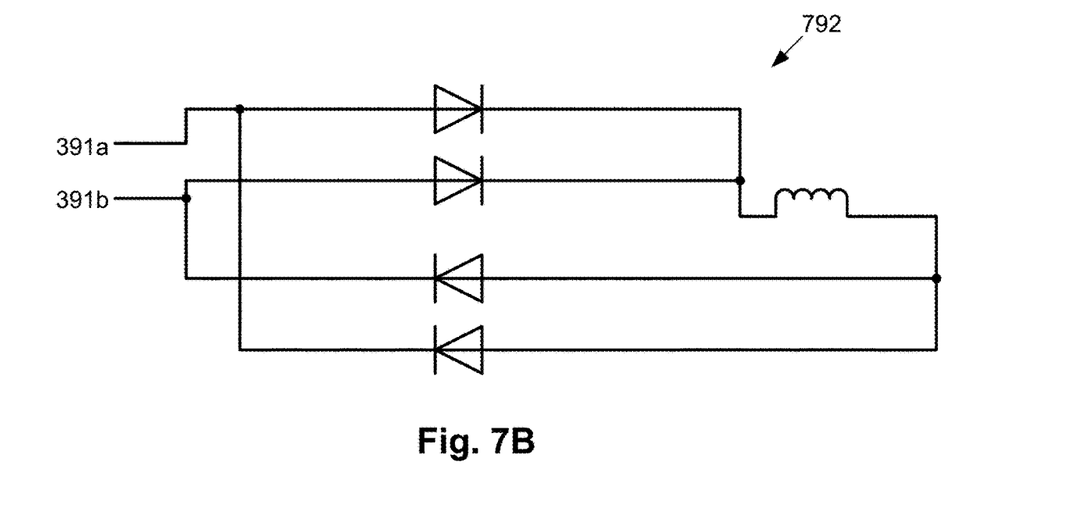
FIG. 7B is a circuit diagram of another embodiment of a phantom utilizing a full wave rectifier, according to the invention.

FIG. 7A illustrates an alternative PCB implementation of a phantom 792 with a full-wave rectifier circuit. Only the balanced receiver of the phantom 792 is shown, and there is no low-pass filtering capacitor implemented in this embodiment, but can be included. The two vias 620 are coupled to the distributed conductance arrangement of a PCB similar to the vias 620 illustrated in FIG. 6D. (The other two vias are illustrated of routing purpose only as indicated by the dotted line in FIG. 7A.) One feature of the illustrated embodiment is nearly ideal compensation of all stray magnetic fields due to the AM carrier in the balanced excitation leads before the rectified node. FIG. 7B illustrates another embodiment of phantom 792 with a full-wave rectifier receiver circuit that can be used with a PCB similar to the embodiment illustrated in FIGS. 6A to 6D.

In at least some embodiments, the demodulation circuit of the phantom can be implemented using any of a variety of circuit topologies, such as those illustrated in FIGS. 3A, 3B, and 6A to 6D, and may include additional circuits or circuit components to provide improvements to the efficiency, noise rejection, linearity, or the like. In at least some embodiments, a simple AM rectifier circuit, such as that illustrated in FIGS. 3A and 3B, employs a very small number of passive components, all of which can be acquired with nonmagnetic packaging. More sophisticated demodulators may utilize more components, although such components may introduce stray fields.

At least some embodiment address the distributed return conductance of the PCB-based phantom. As illustrated in FIGS. 6A to 6D, a PCB-based phantom can be implemented with a conductive sheet, which is may be embodied by, for example, a copper "pour" layer in a PCB fabrication process. However, other alternatives can be used including, but not limited to, patterned layers to modify the sheet resistance, holes in the PCB to reduce thermal magnetic noise, different copper weights for the conductive layers, or metal conductive layers using higher resistance materials than copper, or any combination thereof. In at least some embodiments, such arrangements may eliminate the use of a discrete component resistor 624 (FIG. 6D).

Figure 6E:
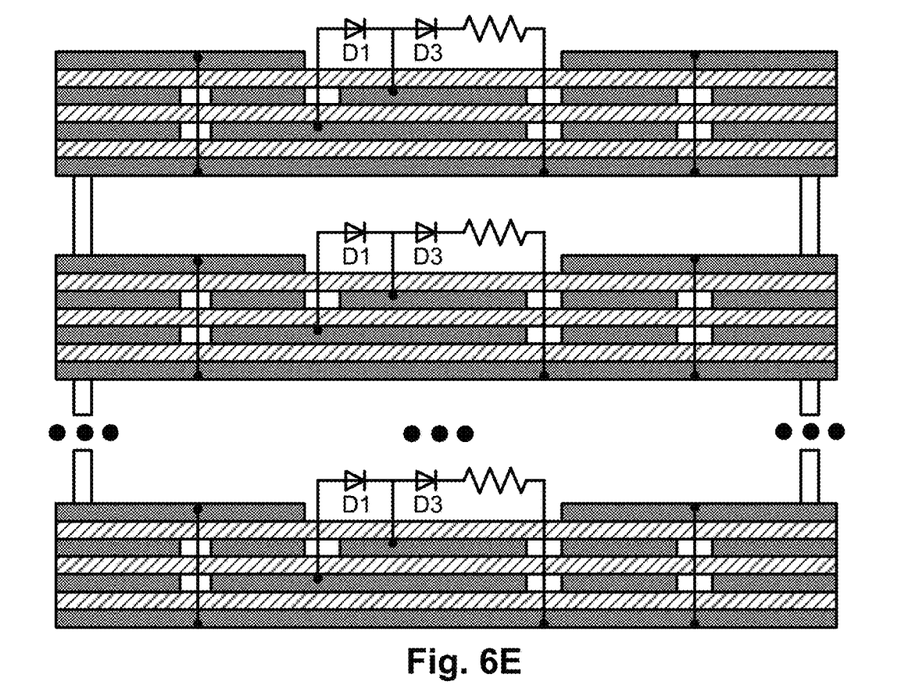
FIG. 6E schematically illustrates a stack of the phantoms of FIG. 6D, according to the invention.

Another embodiment includes a stack of dry PCB phantom boards, each with a conductive sheet layer, that are assembled with interconnection of the pour layers (e.g., conductive layers) between adjacent boards, to better facilitate a 3D volumetric return conductance in a dry environment. A full 3D "phantom brain" could be thus approximated by slices, each implemented on PCB. For example, FIG. 6E illustrates a stack of multiple PCB-based phantoms of the type illustrated in FIG. 6D.

In at least some embodiments, multi-channel operation can be facilitated by the use of balanced conductive transmission lines or wires which can scale to large channel counts. In at least some embodiments, high channel counts in the electronic implementation embodiments can be enabled because the conductor wires can be routed arbitrarily through the phantom volume as the conductor wires produce no detectable stray magnetic field regardless of their position. This is compared with traditional dry phantoms, which require all excitation leads to pass through the spherical center—a condition difficult to approximate with a large numbers of conductors.

In at least some embodiments, with some loss of fidelity to the volumetric return currents in biologically accurate neural circuits, a simple planar-geometry dry MEG phantom, as described herein, can enable complex spatiotemporal magnetic field generation with an inexpensive, quickly produced printed circuit board.

In at least some embodiments, higher fidelity to biological accuracy in the electronic phantom embodiments described herein can be enabled by stacking multiple boards as a dry phantom that can approximate a full brain via PCB slices. Even higher fidelity to biological accuracy can be enabled by immersing the phantom boards in a true volumetric conductive medium, after suitable encapsulation of the electronics. In both of these cases, the disclosed modulation/demodulation architecture allows for 3D stacking without concern for the conductor wire routing.

Figure 8:
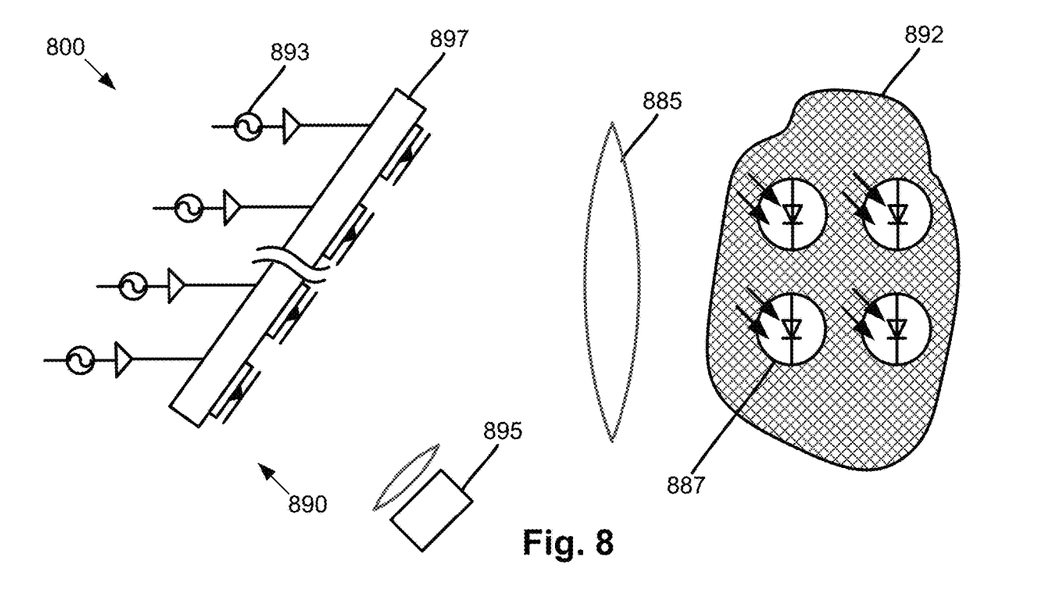
FIG. 8 is a schematic diagram of one embodiment of a phantom device utilizing an optical carrier wave, according to the invention.

At least some embodiments utilize an optical implementation. FIG. 8 illustrates one embodiment of an optical phantom device 800. In a driver 890, one or more low-frequency simulated neural signals, generated by one or more signal sources 893, are mixed with an optical carrier wave, from a light source 895 (or other optical carrier wave source), using modulator 897, such as for example, a spatial light modulator, digitally-controlled projector, or other suitable electro-optical device, to produce a modulated optical signal. Any suitable light source can be used including, but not limited to, visible white light sources, RGB light sources, or the like.

The spatial modes of the modulated optical signal are imaged, via suitable optics 885, onto optical detectors 887 (such as photodiodes) on a phantom 892. In at least some embodiments, the light sources 895 can be spectrally tuned and then additional optical filtering can be added at the optical detectors 887 to address a densely-packed array of optical detectors with light that is color-coded to be filtered out at neighboring optical detectors.

While in transit between the driver 890 and the phantom 892, the wireless modulated optical signal generates no spurious magnetic field that will be detected by the MEG sensors (e.g., OPMs or other magnetometers). At the phantom 892, each optical detector 887 (which could be as simple as a bare photodiode or can be any other suitable optical receiver) rectifies the modulated optical signal, recovers the stimulated neural signal, and directs the low-frequency simulated neural signal into a desired path to simulate a neuron or group of neurons. The desired path can be any of the paths (e.g., the PCB board implementations) described above with respect to the electronic implementations of a phantom device. The simulated neural signals produce the desired magnetic field which can be detected or observed by the MEG sensors. As in some of the electronic implementation embodiments, in at least some optical embodiments, the distributed return current can be facilitated either with a 2D sheet conductance on a layer of the photodetector array board, or by immersing the phantom board in a conductive volume after suitable encapsulation of the photodiodes, except for their terminals.

An advantage of at least some embodiments of the optical implementation is the ability to scale the channel count easily into the thousands or more without encountering wiring harness challenges because the modulated signals are conveyed optically. Using a digitally-programmable modulator (such as an image projector) a phantom device 800 can be scaled into the thousands of channels without encountering wiring difficulties. In at least some embodiments, the phantom device 800 comprises at least 50, 100, 200, 500, 1000, 2000, 5000, 10,000, or more channels. In at least some embodiments, each of the channels are independent channels. The volume return currents can be implemented on the phantom board with dry 2D conductive pours, or—after suitable encapsulation—by immersing the phantom board in a conductive fluid such as saline.

Figure 9:
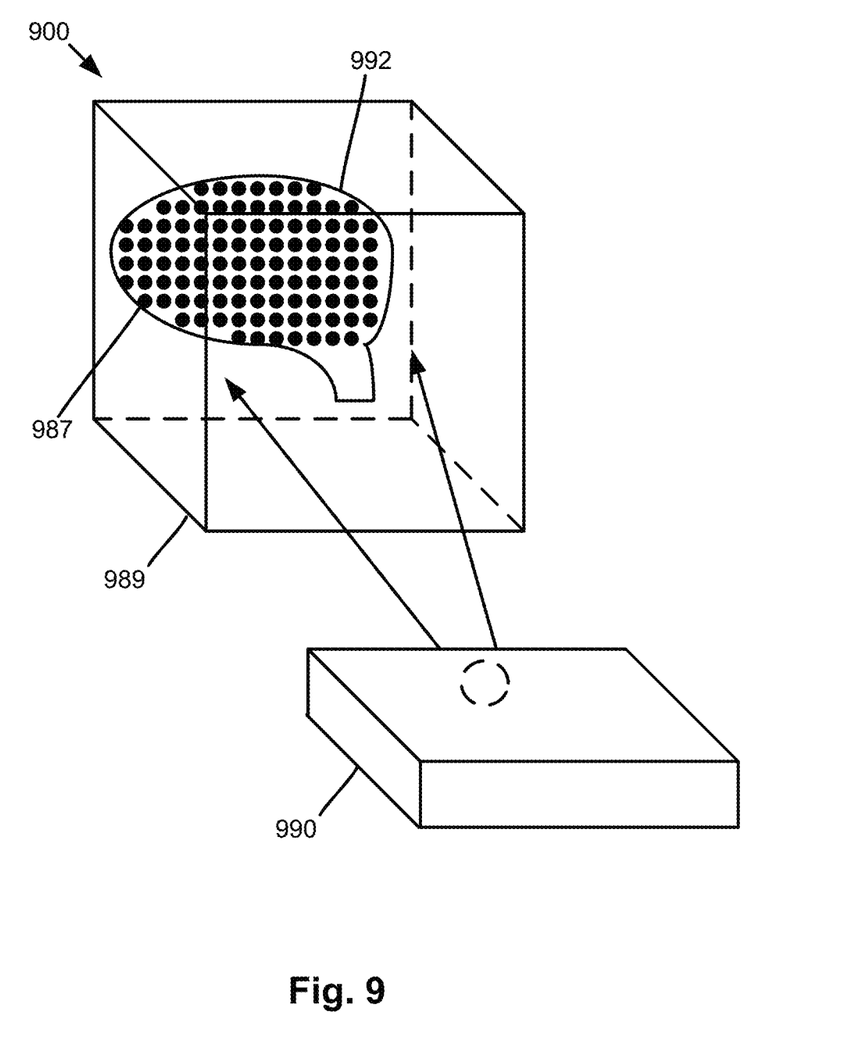
FIG. 9 is a schematic diagram of another embodiment of a phantom device utilizing an optical carrier wave, according to the invention.

FIG. 9 provides another embodiment of an optical phantom device 900 with a driver/controller 990 (such as an optical projector which may be coupled to, or include, a computer or other processor) and a phantom 992 with an array of optical detectors 987 (such as photodiodes). In this embodiments, the array of optical detectors 987 has a biological form (2D or 3D) and the light is transmitted through a transparent medium 989 that can simulate the electrical conductivity of the head (e.g., the scalp, skull, cerebral-spinal fluid, and the like.)

In at least some embodiments, multi-channel operation is facilitated by spatial optical mode addressing, such as can be implemented by, for example, a digital projector or spatial light modulator. This approach may scale to very high channel counts, with potential limitations set by the imaging optics, and the addressing of multiple stacked layers of opaque phantom boards with unidirectional optical excitation. In at least some embodiments, very high channel counts in the optical implementation embodiments are enabled by wireless excitation, and the ready availability of multichannel spatial light modulators.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A neural phantom device configured and arranged to produce a magnetic field to simulate a neural signal, the neural phantom device comprising:
    a driver comprising
        a signal source configured to produce a simulated neural signal, and
        a carrier wave source configured to produce a carrier wave having a frequency of at least 250 Hz,
        wherein the driver is configured to modulate the simulated neural signal using the carrier wave to generate a modulated signal; and
    a phantom configured to receive the modulated signal, demodulate the modulated signal to recover the simulated neural signal, and generate the magnetic field in response to the simulated neural signal.

2. The neural phantom device of claim 1, wherein the carrier wave has a frequency of at least 1 kHz.

3. The neural phantom device of claim 1, wherein the phantom comprises a rectifier circuit.

4. The neural phantom device of claim 1, wherein the phantom comprises a full wave rectifier circuit.

5. The neural phantom device of claim 1, wherein the phantom comprises a printed circuit board and electrical components coupled to the printed circuit board.

6. The neural phantom device of claim 1, wherein the phantom comprises a plurality of printed circuit boards stacked together and electrical component coupled to the printed circuit boards.

7. The neural phantom device of claim 1, wherein the neural phantom device comprises a plurality of the phantoms.

8. The neural phantom device of claim 7, wherein the neural phantom device comprises a plurality of the drivers, wherein each driver is coupled to at least one of the phantoms.

9. A magnetic field measurement system, comprising:
    the neural phantom device of claim 1;
    at least one magnetometer;
    at least one memory; and
    at least one processor coupled to the at least one memory, the at least one magnetometer, and the neural phantom device.

10. The magnetic field measurement system of claim 9, wherein the processor is configured to perform actions comprising:
    operating the neural phantom device to produce at least one simulated neural signal and generate a magnetic field using the phantom of the neural phantom device in response to the simulated neural signal; and
    receiving, from at least one of the at least one magnetometer, a signal in response to the generated magnetic field.

11. A neural phantom device configured and arranged to produce a magnetic field to simulate a neural signal, the neural phantom device comprising:
    a driver comprising
        a signal source configured to produce a simulated neural signal, and
        an optical carrier wave source configured to produce an optical carrier wave,
        wherein the driver modulates the simulated neural signal using the optical carrier wave to generate a modulated optical signal; and
    a phantom configured to receive the modulated optical signal, demodulate the modulated optical signal to recover the simulated neural signal, and generate the magnetic field in response to the simulated neural signal.

12. The neural phantom device of claim 11, wherein the driver comprises an electro-optical modulator.

13. The neural phantom device of claim 11, wherein the driver comprise an optical projector.

14. The neural phantom device of claim 11, wherein the phantom comprises an array of optical detectors.

15. The neural phantom device of claim 14, wherein the optical detectors are photodiodes.

16. The neural phantom device of claim 11, wherein the neural phantom device comprises at least 100 channels.

17. The neural phantom device of claim 11, further comprising a transparent medium disposed between the driver and the phantom, wherein the transparent medium is configured to simulate a conductivity of components of a user's head.

18. The neural phantom device of claim 11, wherein the optical carrier wave source is a light source.

19. A magnetic field measurement system, comprising:
    the neural phantom device of claim 11;
    at least one magnetometer;
    at least one memory; and
    at least one processor coupled to the at least one memory, the at least one magnetometer, and the neural phantom device.

20. The magnetic field measurement system of claim 19, wherein the processor is configured to perform actions comprising:
    operating the neural phantom device to produce at least one simulated neural signal and generate a magnetic field using the phantom of the neural phantom device in response to the simulated neural signal; and
    receiving, from at least one of the at least one magnetometer, a signal in response to the generated magnetic field.

* * * * *